United States Patent [19]

Lang et al.

[11] Patent Number: 4,970,063
[45] Date of Patent: Nov. 13, 1990

[54] SALTS OF THIAMORPHOLINONE CARBOXYLIC ACID WITH 2,4-DIAMINOPYRIMIDINE DERIVATIVES AND THEIR USE IN COSMETICS AND PHARMACEUTICALS

[75] Inventors: Gerard Lang, Saint-Gratien; Jean Maignan, Tremblay-les-Gonesse; Serge Restle, Aulnay-sous-Bois, all of France

[73] Assignee: L'Oreal, Paris, France

[21] Appl. No.: 225,818

[22] Filed: Jul. 29, 1988

[30] Foreign Application Priority Data

Jul. 31, 1987 [LU] Luxembourg ............................ 86958

[51] Int. Cl.$^5$ .................... A61K 31/54; C07D 417/14
[52] U.S. Cl. .................................. 424/47; 514/227.5; 544/58.2; 544/323
[58] Field of Search ...................... 514/227.5; 424/47; 544/58.2, 323

[56] References Cited

U.S. PATENT DOCUMENTS

| | | | |
|---|---|---|---|
| 3,461,461 | 8/1969 | Anthony et al. | 544/325 |
| 4,139,619 | 2/1979 | Chidsey | 514/235.8 |
| 4,539,320 | 9/1985 | Lang et al. | 514/227.5 |

FOREIGN PATENT DOCUMENTS

| | | |
|---|---|---|
| 0211268 | 2/1987 | European Pat. Off. . |
| 2525220 | 10/1983 | France . |
| 2032434 | 5/1980 | United Kingdom . |
| 2118553 | 11/1983 | United Kingdom . |

OTHER PUBLICATIONS

Noser et al., "Chemical Abstracts", vol. 108, 1988, Col. 108: 43835s.

*Primary Examiner*—Glennon H. Hollrah
*Assistant Examiner*—James H. Turnipseed
*Attorney, Agent, or Firm*—Fleit, Jacobson, Cohn, Price, Holman & Stern

[57] ABSTRACT

A compound has the following composition:

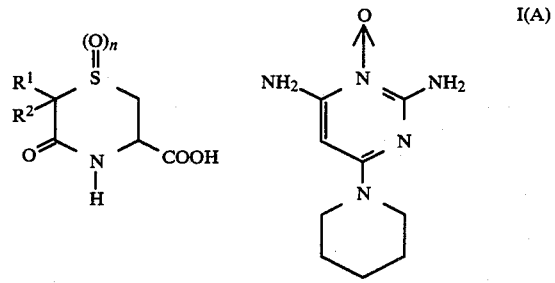

or its corresponding ionic form:

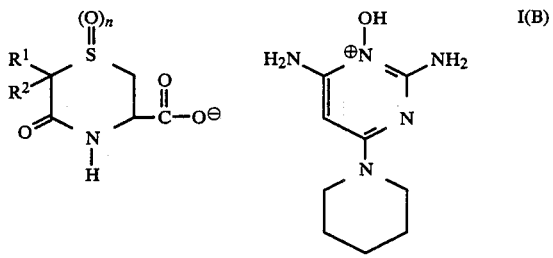

wherein:
n equals 0, 1 or 2, and
$R_1$ and $R_2$ may be identical or different and represent a hydrogen atom or a linear or branched low alkyl radical having 1 to 6 carbon atoms.

11 Claims, No Drawings

SALTS OF THIAMORPHOLINONE CARBOXYLIC ACID WITH 2,4-DIAMINOPYRIMIDINE DERIVATIVES AND THEIR USE IN COSMETICS AND PHARMACEUTICALS

BACKGROUND OF THE INVENTION

1. Field of the invention 2,4-diaminopyrimidines, particularly 6-piperidino-2,4-diaminopyrimidine-3-oxide which is known by the name "Minoxidil", are well known in the art. This product is used in human therapeutics particularly for its antihypertensive properties and for topical application in the treatment of baldness and alopecia.

2. Description of the prior art

A disadvantage of "Minoxidil" is that it is practically insoluble in water which limits its use in that formulations having relatively low proportions of water and containing high concentrations of alcohol or polyol are in general not well tolerated.

However, certain salts of "Minoxidil" are known, in particular the sulfate, the 4-N-acylthiazolidine carboxylate and the L-5-oxoproline salt.

SUMMARY OF THE INVENTION

The applicants have discovered, and this forms the object of the invention, that thiamorpholinone carboxylic acid salts of "Minoxidil" are particularly interesting.

Thiamorpholinone carboxylic acids are known as described in the applicants French patent No. FR-2 525 220.

These acids are primarily known for their moisturizing and emollient properties.

Salts of thiamorpholinone carboxylic acid with 2,4-diaminopyrimidine derivatives in accordance with the invention have shown themselves to be particularly soluble in aqueous media thus overcoming the disadvantages of the previous formulations, especially concerning their tolerance by the organism.

In addition the salts are active both to cause hair regrowth and to treat seborrhoea. These properties mean that they are particularly appropriate for scalp treatment, especially treatment for hair loss but also for alopecia, more particularly alopecia aerata and pattern alopecia, desquamating dermatitis, etc...

Thus an object of the invention is to provide new salts of 2,4-diaminopyrimidine derivatives constituted by salts of thiamorpholinone carboxylic acid.

Cosmetic or pharmaceutical compositions based on these salts constitute a further object of the invention.

Another object of the invention is a process for the treatment of baldness using such salts.

Other objects of the invention will become apparent from the description and the following examples.

Salts according to the invention are primarily characterized in that they correspond to the formula:

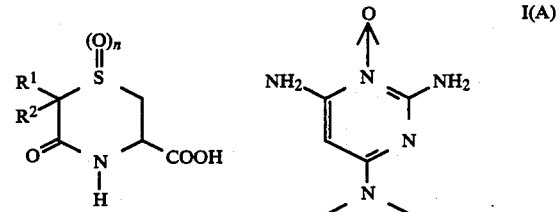

or to its corresponding ionic form:

where:
n equals 0, 1 or 2 and
$R_1$ and $R_2$ may be identical or different and represent a hydrogen atom or a straight or branched chain low alkyl radical having 1 to 6 carbon atoms.

"Low alkyl radical" preferably means methyl, ethyl, propyl, isopropyl, butyl, pentyl or hexyl. Particularly preferred compounds according to the invention are
3-thiamorpholinone-5-carboxylate-6-piperidino-2,4-diaminopyrimidine-3-oxide;
2-methyl-3-thiamorpholinone-5-carboxylate-6-piperidino-2,4-diaminopyrimidine-3-oxide;
2,2-dimethyl-3-thiamorpholinone-5-carboxylate-6-piperidino-2,4-diaminopyrimidine-3-oxide;
1-oxo-3-thiamorpholinone-5-carboxylate-6-piperidino-2,4-diaminopyrimidine-3-oxide;
1,1-dioxo-3-thiamorpholinone-5-carboxylate-6-piperidino-2,4-diaminopyrimidine-3-oxide;
1-oxo-2-methyl-3-thiamorpholinone-5-carboxylate-6-piperidino-2,4-diaminopyrimidine-3-oxide;
1-oxo-2,2-dimethyl-3-thiamorpholinone-5-carboxylate-6-piperidino-2,4-diaminopyrimidine-3-oxide; and
2-hexyl-3-thiamorpholinone-5-carboxylate-6-piperidino-2,4-diaminopyrimidine-3-oxide.

Compositions conforming to the invention intended for topical application are primarily characterized in that they contain 0.1 to 10% by weight of a compound having formula (I) and preferably 0.5 to 5% by weight with respect to the total composition weight in an aqueous medium appropriate for topical application.

In particular the compositions may be in the form of lotions, creams or gels and may if necessary be packaged as aerosols.

As well as the active agent having formula (I) these compositions may contain other ingredients which are in standard use in cosmetic or pharmaceutical formulations intended for topical application.

In particular they may contain glycerol, urea or lactic acid, also thickening agents, surface-active agents and solvents which are acceptable in the cosmetic and pharmaceutical fields, for example low alcohols such as ethanol or isopropanol, ethyleneglycol, monomethyl, monoethyl or monobutyl ethers of ethyleneglycol, propyleneglycol and monomethyl ethers of propyleneglycol or dipropyleneglycol.

The compositions may also contain other active agents, particularly cosmetic agents such as thaimorpholinone, 5-benzylcysteamine and its derivatives, or tioxolone.

The applicant has discovered that an aqueous composition with increased tolerance for topical application can be prepared using compounds according to the invention.

The concentrations of active material can also be reduced due to the increased biological availability of the salts according to the invention.

In addition, these compositions have the advantage of possessing better cosmetic properties, since treatment compositions do not coat the hair and can be rinsed out more easily.

Finally, they are far less irritating to the skin and eyes and less toxic.

A further object of the invention consists in a method for cosmetic treatment of baldness to induce and stimulate hair growth or reduce its loss and combat seborrhea.

This method consists in applying the compositions described above to alopecic areas of bald skin and to an individual's hair.

A composition may be applied after washing the bald area and hair with shampoo or shortly after shampooing, for example.

Compounds according to the invention are prepared either by adding an alcoholic solution of the thiamorpholinone carboxylic acid to a previously prepared alcoholic solution containing an equivalent quantity of 6-piperidino-2,4-diaminopyrimidine-3-oxide then concentrating the mixture until the onset of crystallization and freezing the whole;

or by adding an equivalent quantity of solid thiamorpholinone carboxylic acid to a suspension of 6-piperidino-2,4-diaminopyrimidine-3-oxide in water. In this latter case, very high concentrations are used and the salt is drained and dried.

The following examples are intended to illustrate the invention without in any way limiting its scope.

EXAMPLE 1

Synthesis of the salt of 3-thiamorpholinone-5-carboxylic acid and 6-piperidino-2,4-diaminopyrimidine-3-oxide A solution of 3.80 g of 3-thiamorpholinone-5-carboxylic acid in 70 cm$^3$ of boiling methanol was added to a solution of 5 g of 6-piperidino-2,4-diaminopyrimidine-3-oxide in 300 cm$^3$ of hot methanol.

6.7 g of product was recovered whose $^1$H NMR spectrum agreed with the expected structure.

| | Elemental analysis: $C_{14}H_{22}N_6O_4S$ | | | | |
|---|---|---|---|---|---|
| | C % | H % | N % | O % | S % |
| Theory | 45.39 | 5.99 | 22.69 | 17.28 | 8.65 |
| Found | 45.44 | 5.94 | 22.62 | 17.45 | 8.81 |

EXAMPLE 2

Synthesis of the salt of 3-thiamorpholinone-5-carboxylic acid and of 6-piperidino-2,4-diaminopyrimidine-3-oxide 0.770 g of 3-thiamorpholinone-5-carboxylic acid was added to a suspension of 1 g of 6-piperidino-2,4-diaminopyrimidine-3-oxide in 10 cm$^3$ of water, agitated for one hour and left overnight.

The product was filtered and dried under vacuum.

After recrystallization from methanol a white product was obtained which melted at 205° C. and whose $^1$H NMR conformed to the structure of the salt obtained in Example 1.

EXAMPLE 3

Synthesis of the salt of 2-methyl-3-thiamorpholinone-5-carboxylic acid and 6-piperidino-2,4-diaminopyrimidine-3-oxide A solution of 4.18 g of 2-methyl-3-thiamorpholinone-5-carboxylic acid in a minimum of boiling methanol was added to a solution of 5 g of 6-piperidino-2,4-diaminopyrimidine-3-oxide in 300 cm$^3$ of hot methanol.

The methanol was evaporated off under reduced pressure and the desired salt crystallized from ether.

Recrystallisation from an isopropanol/ diisopropyl ether mixture yielded 6.65 g of the salt of 2-methyl-3-thiamorpholinone-5-carboxylic acid and 6-piperidino-2,4-diaminopyrimidine-3-oxide whose fusion point was 129°–130° C.

| | Elemental analysis: $C_{15}H_{24}N_6O_4S$ | | | | |
|---|---|---|---|---|---|
| | C % | H % | N % | O % | S % |
| Theory | 46.86 | 6.29 | 21.86 | 16.65 | 8.34 |
| Found | 46.63 | 6.31 | 21.69 | 16.87 | 8.20 |

EXAMPLE 4

Synthesis of the salt of 2,2-dimethyl-3-thiamorpholinone -5-carboxylic acid and of 6-piperidino-2,4-diaminopyrimidine-3-oxide A solution of 1 g of 2,2-dimethyl-3-thiamorpholinone-5-carboxylic acid in a minimum of boiling methanol was added to a solution of 1.10 g of 6-piperidino-2,4-diaminopyrimidine-3-oxide in about 100 cm$^3$ of hot methanol.

The methanol was evaporated off under reduced pressure and the desired salt crystallized from ether.

Recrystallisation from an isopropanol/ diisopropyl ether mixture yielded 1.16 g of the salt of 2,2-dimethyl-3-thiamorpholinone-5-carboxylic acid and 6-piperidino-2,4-diaminopyrimidine-3-oxide whose fusion point was 160°–161° C.

| | Elemental analysis: $C_{16}H_{26}N_6O_4S$ | | | | |
|---|---|---|---|---|---|
| | C % | H % | N % | O % | S % |
| Theory | 48.22 | 6.58 | 21.09 | 16.06 | 8.05 |

EXAMPLE 5

Synthesis of the salt of 3-thiamorpholinone-1-oxide-5-carboxylic acid and of 6-piperidino-2,4-diaminopyrimidine-3-oxide A solution of 4.23 g of 3-thiamorpholinone-1-oxide-5-carboxylic acid in a minimum of boiling methanol was added to a solution of 5 g of 6-piperidino-2,4-diaminopyrimidine-3-oxide in 80 cm³ of hot methanol.

The reaction mixture was concentrated and allowed to cool. The desired salt crystallized out as white crystals whose fusion point (with decomposition) was 180° C.

| Elemental analysis: $C_{14}H_{22}N_6O_5S$ | | | | |
|---|---|---|---|---|
| C % | H % | N % | O % | S % |
| Theory  43.51 | 5.74 | 21.75 | 20.70 | 8.30 |
| Found   43.42 | 5.77 | 21.96 | 20.84 | 8.27 |

EXAMPLE 6

Synthesis of the salt of 3-thiamorpholinone-1-dioxide-5-carboxylic acid and of 6-piperidino-2,4-diaminopyrimidine-3-oxide A solution of 4.61 g of 3-thiamorpholinone-1-dioxide-5-carboxylic acid in a minimum of boiling methanol was added to a solution of 5 g of 6-piperidino-2,4-diaminopyrimidine-3-oxide in 80 cm³ of hot methanol.

The reaction mixture was concentrated to about 75 cm³ and allowed to cool. The product was filtered, washed with cold methanol and dried. The desired salt crystallized in the form of white crystals whose fusion point (with decomposition) was 175° C.

| Elemental analysis: $C_{14}H_{22}N_6O_6$ | | | | |
|---|---|---|---|---|
| C % | H % | N % | O % | S % |
| Theory  41.78 | 5.51 | 20.88 | 23.85 | 7.97 |
| Found   41.77 | 5.47 | 21.11 | 23.96 | 8.07 |

EXAMPLES OF FORMULATIONS

Three active lotions for stimulating hair growth were prepared having the following compositions:

EXAMPLE 1

| | |
|---|---|
| Salt of 3-thiamorpholinone-5-carboxylic acid and 6-piperidino-2,4-diaminopyrimidine-3-oxide | 0.85 g |
| Heteropolysaccharide sold by RHONE-POULENC under the name RHODOPOL 23 | 1.00 g |
| Preservative qs | |
| Water qsp | 100.00 g |

EXAMPLE 2

| | |
|---|---|
| Salt of 2-methyl-3-thiamorpholinone-5-carboxylic acid and 6-piperidino-2,4-diaminopyrimidine-3-oxide | 5.00 g |
| Reticulated polyacrylic acid, Mol. Wt = 3,000,000, sold by GOODRICH under the name CARBOPOL 934 | 1.00 g |
| 2-amino-2-methyl-1-propanol qsp pH = 7.5 | |
| Water qsp | 100.00 g |

EXAMPLE 3

| | |
|---|---|
| Salt of 3-thiamorpholinone-1-oxide-5-carboxylic acid and 6-piperidino-2,4-diaminopyrimidine-3-oxide | 2.50 g |
| Hydroxypopylcellulose sold by HERCULES under the name "KLUCELG" | 3.00 g |
| Preservative qs | |
| Water qsp | 100.00 g |

1 to 2 ml of these compositions, in the form of lotions, were applied to the alopecic zone of the bald skin twice a day, penetration being improved using massage.

We claim:

1. A compound having the formula:

I(A)

[structure shown]

or the corresponding ionic formula:

I(B)

[structure shown]

wherein:

n equals 0, 1 or 2 and $R_1$ and $R_2$ may be identical or different and represent a hydrogen atom or a linear or branched low alkyl radical having 1 to 6 carbon atoms.

2. A compound according to claim 1 wherein the low alkyl radical represented by $R_1$ and/or $R_2$ is a methyl, ethyl, propyl, isopropyl, butyl, pentyl or hexyl radical.

3. A compound according to claim 2 wherein the salt is selected from the group consisting of:

3-thiamorpholinone-5-carboxylate-6-piperidino-2,4-diaminopyrimidine-3-oxide;

2-methyl-3-thiamorpholinone-5-carboxylate-6-piperidino-2,4-diaminopyrimidine-3-oxide;

2,2-dimethyl-3-thiamorpholinone-5-carboxylate-6-piperidino-2,4-diaminopyrimidine-3-oxide;

1-oxo-3-thiamorpholinone-5-carboxylate-6-piperidino-2,4-diaminopyrimidine-3-oxide;

1,1-dioxo-3-thiamorpholinone-5-carboxylate-6-piperidino-2,4-diaminopyrimidine-3-oxide;

1-oxo-2-methyl-3-thiamorpholinone-5-carboxylate-6-piperidino-2,4-diaminopyrimidine-3-oxide;

1-oxo-2,2-dimethyl-3-thiamorpholinone-5-carboxylate-6-piperidino-2,4-diaminopyrimidine-3-oxide; and 2-hexyl-3-thiamorpholinone-5-carboxylate-6-piperidino-2,4-diaminopyrimidine-3-oxide.

4. A composition intended for topical application comprising 0.1 to 10%, by weight, with respect to the total weight of the composition, of a compound according to claim 1 in an aqueous medium appropriate to topical application.

5. A composition according to claim 4 in the form of a lotion, cream or gel or packaged as an aerosol.

6. A composition according to claim 5, additionally containing glycerol, urea, lactic acid or solvents.

7. A composition according to claim 6, additionally containing thiamorpholinone, 5-benzylcysteanine and its derivatives or tioxolone.

8. A process for cosmetic treatment of baldness to induce and stimulate hair growth or reduce hair loss, whereby a compound according to claim 1 is applied to the bald area.

9. A pharmaceutical composition for the therapeutic treatment of a condition selected from the group consisting of hair loss, alopecia, desquamating dermatitis and seborrhea comprising a therapeutically effective amount of a compound of claim 1.

10. Method for treating a condition selected from the group consisting of hair loss, alopecia, desquamating dermatitis and seborrhea, comprising applying to the hair or the alopecia area of the bad skin a pharmaceutical composition according to claim 9.

11. A composition according to claim 4, wherein the compound is present in an amount of 0.5 to 5% by weight.

* * * * *